(12) United States Patent
Orchard-Webb

(10) Patent No.: US 6,972,462 B2
(45) Date of Patent: Dec. 6, 2005

(54) COMPACT HIGH VOLTAGE ESD PROTECTION DIODE

(75) Inventor: Jonathan Harry Orchard-Webb, Chepstow (GB)

(73) Assignee: Zarlink Semiconductor AB, Jarfalla (SE)

( * ) Notice: Subject to any disclaimer, the term of this patent is extended or adjusted under 35 U.S.C. 154(b) by 103 days.

(21) Appl. No.: 10/426,450

(22) Filed: Apr. 30, 2003

(65) Prior Publication Data

US 2004/0070005 A1    Apr. 15, 2004

(51) Int. Cl.⁷ ............................................. H01L 29/72
(52) U.S. Cl. ..................... 257/355; 257/356; 257/371; 257/408
(58) Field of Search ............................... 257/355, 356, 257/371, 408

(56) References Cited

U.S. PATENT DOCUMENTS

| | | | |
|---|---|---|---|
| 5,017,985 A * | 5/1991 | Lin | 257/356 |
| 5,162,888 A * | 11/1992 | Co et al. | 257/408 |
| 6,469,353 B1 * | 10/2002 | Amerasekera et al. | 257/356 |
| 6,670,677 B2 * | 12/2003 | Choe et al. | 257/355 |
| 2004/0021180 A1 * | 2/2004 | Salling et al. | 257/371 |

* cited by examiner

*Primary Examiner*—David Nelms
*Assistant Examiner*—Dao H. Nguyen
(74) *Attorney, Agent, or Firm*—Lawrence E. Laubscher, Jr.

(57) ABSTRACT

A protection device provides to integrated circuits against high voltages. The diode includes a diode connected to provide a safe discharge path for the high voltage currents. The diode is configured so that in reverse bias breakdown occurs across an area portion of its active junction. The device can dissipate a large amount of ESD energy in a minimal area.

17 Claims, 4 Drawing Sheets

COMPACT HIGH VOLTAGE ESD PROTECTION DIODE

BACKGROUND OF THE INVENTION

1. Field of the Invention

This invention relates to the field of electrostatic discharge (ESD) protection, and in particular of to an ESD protection diode.

2. Description of Related Art

Protection diodes are used to protect integrated circuits, particularly CMOS circuits, from damage caused by electrostatic discharge. A basic requirement of protection diodes is that the breakdown voltage be greater than the full worst case supply voltage applied to the circuit. For silicon integrated circuits, this voltage is, typically, below 10 Volts. The energy dissipated in a protection diode when it beaks down is related to the breakdown voltage. For example, the energy dissipated in a protection diode for a nominal 350V circuit will be approximately 50 times higher than for a nominal 5V circuit.

There are many protection systems in use today. The most prevalent ones are similar to that shown in FIG. 1, for a p-substrate process. In FIG. 1, diodes D2 to D5 normally operate in the forward mode under ESD stress, but are also required to withstand the full supply voltage in reverse bias. Diode D1, however, may operate in both forward and reverse bias during an ESD Discharge.

Many high voltage processes do not have a complementary high voltage capability and a more sophisticated protection system may be used, as shown in FIG. 2. Here, Diodes D4 and D5 have been removed, making it necessary for diodes D2 and D3 to operate under both forward and reverse bias under ESD stress. Diode D2, the input protection diode is generally a snap back device, operating at a relatively low voltage. Some output protection diodes, D3, would normally operate at high voltage.

There is a therefore a need for protection diodes that are capable of operating at high voltages. In the simple protection system shown in FIG. 1, D1 and D3 would be high voltage diodes.

A problem with conventional protection techniques is that the area needed to dissipate the energy safely when an ESD diode breaks down tends to be very large for high voltages. The limiting factor in presently used protection diodes is the failure arising from the constriction of current flow and heat flow at the junction edge, particularly under reverse bias.

SUMMARY OF THE INVENTION

This invention offers a solution to these problems experienced in the prior art by causing breakdown current in the protection diode to flow through the diode area rather than the perimeter of the device.

According to the present invention there is provided a protection device for providing protection to an integrated circuit against high voltages, comprising a diode connected to provide a safe discharge path, said diode having an active junction and being configured so that in reverse bias breakdown occurs across an area of the active junction at a breakdown voltage that is just above the maximum supply voltage of the integrated circuit.

The protection device in accordance with the invention can have a number of desirable characteristics. In particular, it can have the capability to dissipate a very large pulse of ESD energy into a minimal area; the capability to achieve a reproducible high voltage breakdown; compatibility with standard processing techniques; the capability to achieve a stable breakdown voltage with time and stress; the capability to achieve a low series resistance for the diode with reverse current flow; and the capability to work with the other protection components to form a complete protection system. Other desirable technical aspects of the device are ease of insertion under a bond pad to save area, low leakage after stress, and low noise.

The diode in accordance with the invention uses area, not edge conduction. In one exemplary embodiment, a deep junction is used to inhibit edge breakdown of the active junction and another deep diffusion is used to adjust the breakdown of the whole area of the active junction so that breakdown occurs over the entire diode area at just above the maximum supply voltage.

In another aspect the invention provides a method of making a protection diode for providing protection to an integrated circuit against high voltages, comprising providing a first layer of first conductivity type; forming a source-drain region of a second conductivity type in said first layer; forming a well of said second conductivity type in said first layer to suppress breakdown of said source-drain region; and forming a region of said first conductivity type adjacent said source-drain region to cause said diode to break down across the source-drain region enclosed by the well at just above the maximum supply voltage of the integrated circuit.

BRIEF DESCRIPTION OF THE DRAWINGS

The invention will now be described in more detail, by way of example only, with reference to the accompanying drawings, in which.

DETAILED DESCRIPTION OF THE PREFERRED EMBODIMENTS

The fabrication of a p-substrate process will be described with reference to FIGS. 3a to 3d. It will of course be appreciated by one skilled in the art that the invention is equally applicable to an n-substrate process, in which case the conductivity types are reversed.

Figure 1:
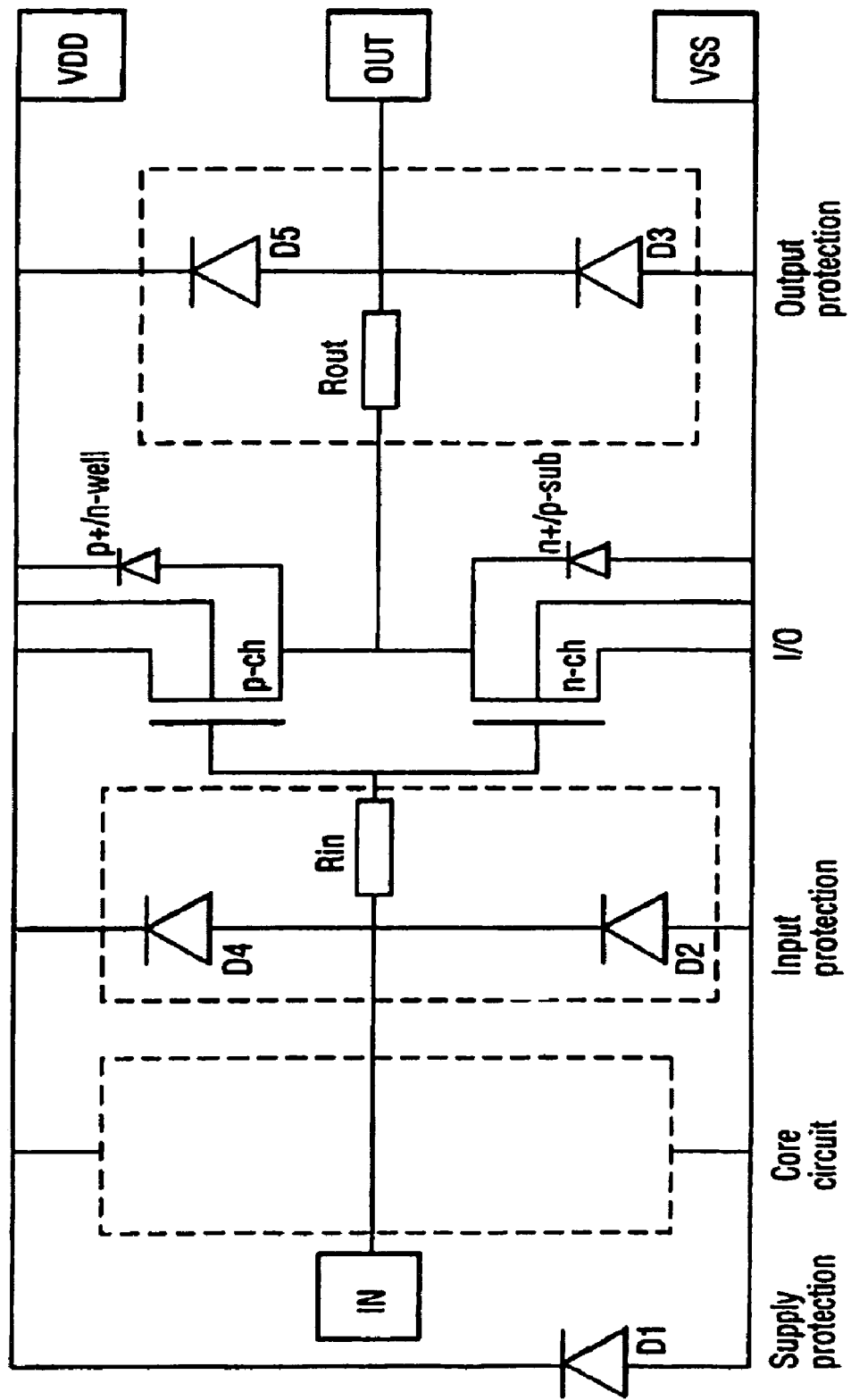
FIG. 1 illustrates a commonly used prior art protection system.
Figure 2:
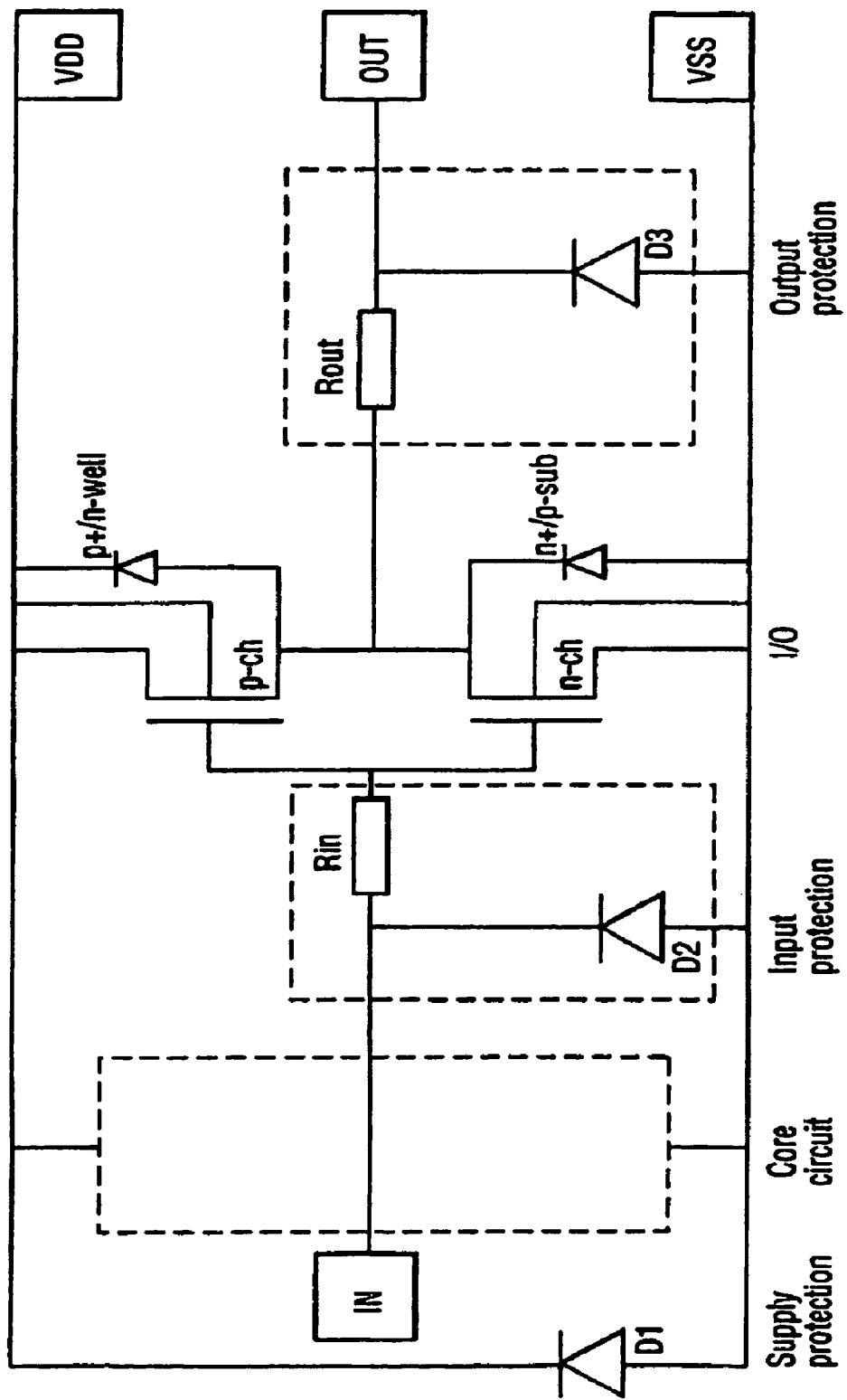
FIG. 2 illustrates a commonly used protection system without diodes to a Vdd rail.
Figure 3:
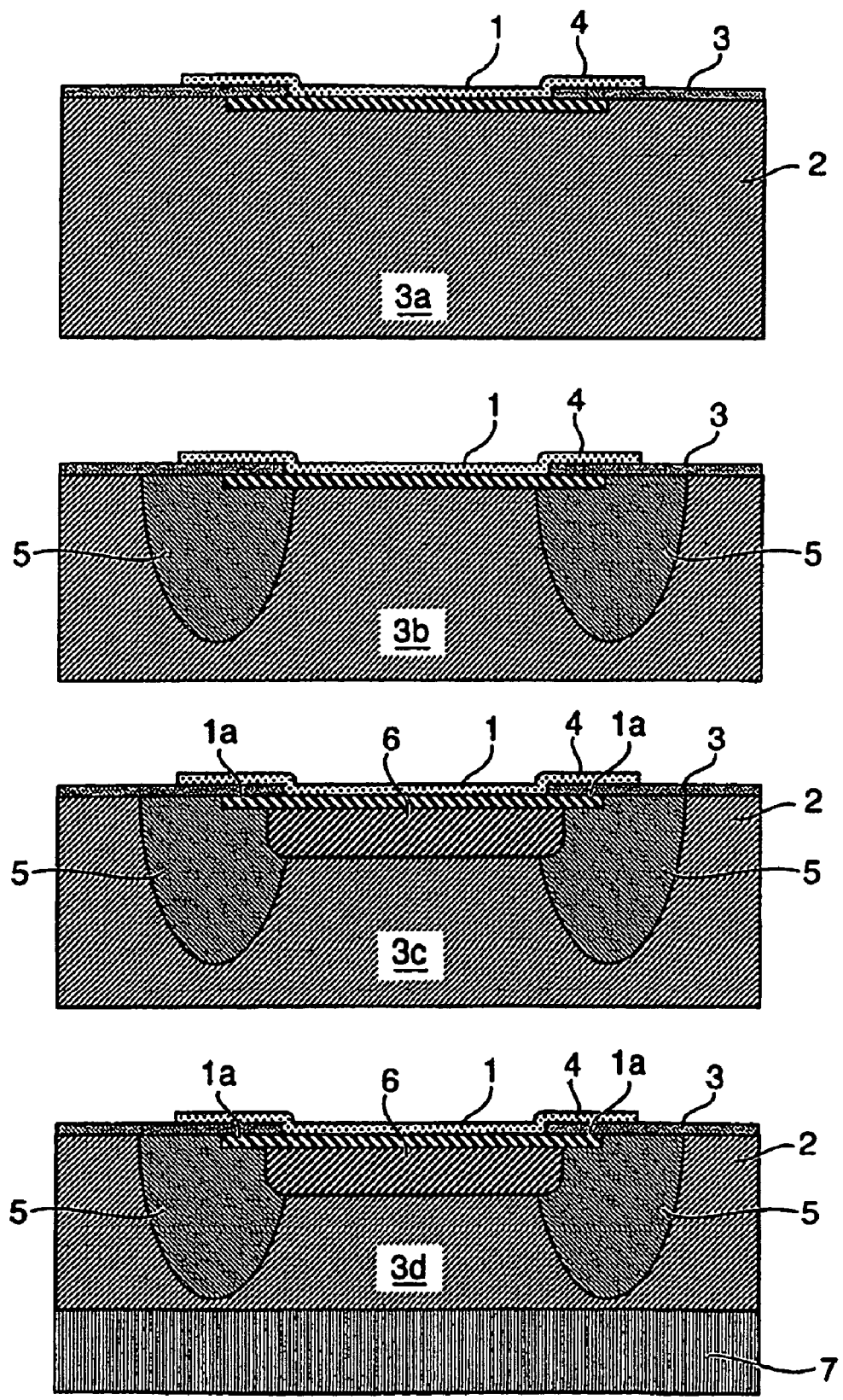
FIGS. 3a to 3d illustrate the fabrication of a p-substrate diode.

In FIG. 3a, a heavily doped n+ source and drain region 1 is diffused into a p-type epitaxial layer 2 in a conventional manner to form a pn junction. The epitaxial layer 2 is covered with an insulator/oxide layer 3 with an opening to receive a metal contact layer 4. This structure would normally break down at an unacceptably low voltage due to corner and edge avalanche effects at the junction of the n+ diffusion region 1 and the p-type layer 2.

In order to suppress breakdown of the n+ diffusion region 1, an n-well 5 is located at the edges 1a of the region 1 by a technique which per se is well known to one skilled in the art. However, even in the presence of the n-well 5, breakdown will eventually occur due to edge breakdown of the n-well. This breakdown voltage is, typically, too high for protection purposes, and does not offer a low resistance path for ESD current.

As shown in FIG. 3c, in this exemplary embodiment of the invention, a p-type ion implant region 6 is formed below the n+ diffusion region 1 between the n-wells 5 to modify the breakdown voltage. The p-type implant region 6 is formed by ion implantation and extends into the n-well 5 to cause the diode to break down across the n+ area 1 enclosed by the n-well 5. The region 6 can alternatively be formed as a deep diffusion.

Figure 4:
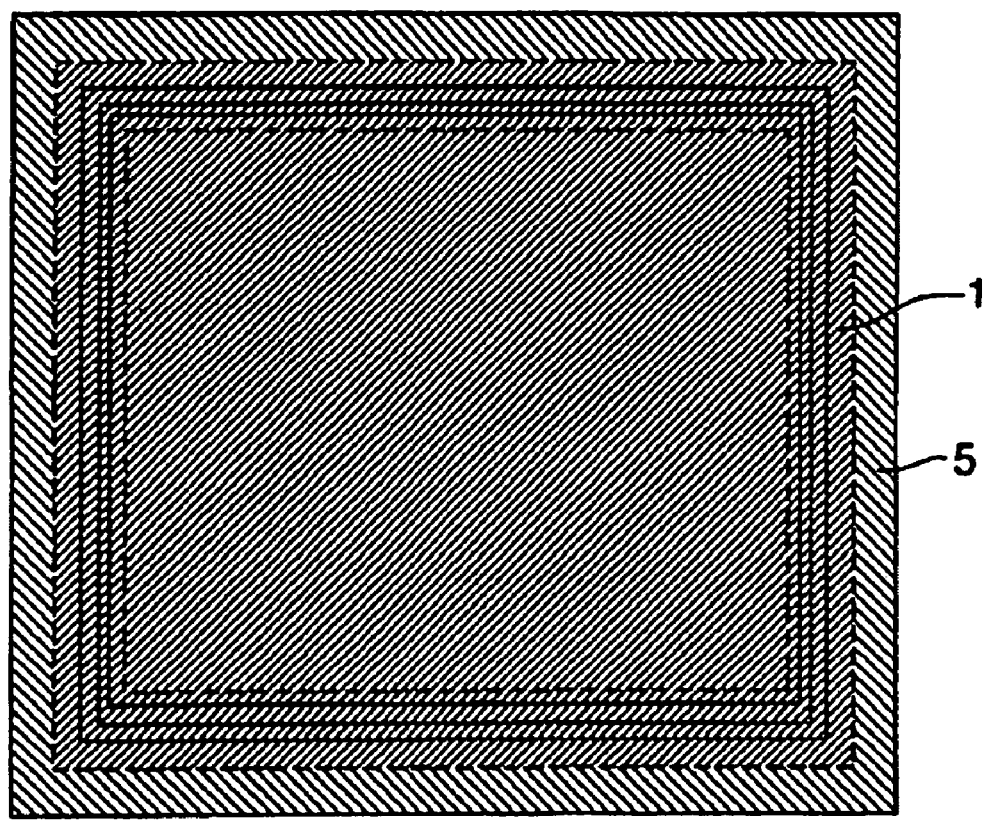
FIG. 4 is a plan view of a p-substrate diode.

As shown in FIG. 3d, a heavily doped substrate 7 can be employed under the epitaxial layer 2 to lower the diode series resistance. FIG. 4 shows a plan view of the diode in FIG. 3d.

The described diode is adapted for p-type substrate processes. It can easily be adapted to n-type substrate processes by reversing the conductivity type of each region. For example, the source drain region 1 becomes a p+ region, and the implanted region 6 becomes an n-type region, and so on.

The diode can be made from a range of diffusions generated uniquely for the diode. This is, however, wasteful in many applications. For most processes it is sufficient to use the n-well diffusion, and in some processes, a diffusion, such as a transistor base or resistor diffusion may meet the requirements for the voltage adjusting p diffusion.

It is best, in most applications, to use the special implant for the p region 6 to provide the optimum breakdown voltage.

The diode is preferably drawn partly under a bond pad. This has advantages of saving area, promoting uniform current flow and storing ESD heat energy in the ball bond of the bond pad. Less ideally, the diode could be placed anywhere on the chip, subject to latch-up constraints.

While the diode has been developed specifically with ESD protection in mind, it can be adapted to other applications where reliable high voltage on-chip diodes are required. Extension to other technologies is also possible. A possible application would be the newly emerging SiC technologies. The diode can also be adapted for use on high voltage bipolar processes.

What is claimed is:

1. A protection device for providing protection against high voltages to an integrated circuit having a maximum supply voltage, comprising:
    a diode connected to provide a safe discharge path, said diode having a first region of first conductivity type located in a second region of second conductivity type to form an active junction with edges, and a well of said first conductivity type located at the edges of said first region to suppress edge breakdown of said active junction, and said diode being configured so that in reverse bias breakdown occurs across an area of the active junction enclosed by said well at a breakdown voltage that is at just above the maximum supply voltage of the integrated circuit.

2. A protection device as claimed in claim 1, wherein said diode is configured so that breakdown occurs over substantially the entire diode area enclosed by said well.

3. A protection device as claimed in claim 1, wherein said diode has a third region below said first region in the area enclosed by the well to adjust the breakdown voltage of the active junction.

4. A protection device as claimed in claim 3, wherein said third region is an ion implant region.

5. A protection device as claimed in claim 3, wherein said third region is of said second conductivity type.

6. A protection device as claimed in claim 5, wherein said second region is an epitaxial layer.

7. A protection device as claimed in claim 6, further comprising a substrate of said second conductivity type under said epitaxial layer.

8. A protection device as claimed in claim 6, wherein said first region has enhanced doping relative to said well.

9. A protection device as claimed in claim 8, wherein said first region is n+ type, said well is n-type and said region is p-type.

10. A protection device as claimed in claim 9, wherein said first region is p+ type, said well is p-type and said second region is n-type.

11. An integrated circuit having a maximum supply voltage and comprising at least one protection diode to provide protection against high voltages, said protection diode having a first region of first conductivity type located in a second region of second conductivity type to form an active junction with edges, and a well located at the edges of said first region to suppress edge breakdown of said active junction, and said diode being configured so that in reverse bias, breakdown occurs across an area of the active junction enclosed by said well at a breakdown voltage that is just above the maximum supply voltage of the integrated circuit.

12. An integrated circuit as claimed in claim 11, wherein the diode is formed at least partly under a bond pad.

13. An integrated circuit as claimed in claim 11, wherein a third region is formed below said first region in the area enclosed by the well to promote breakdown of the active junction in reverse bias across said area enclosed by the well.

14. An integrated circuit as claimed in claim 13, further comprising a heavily doped substrate below said second region.

15. An integrated circuit protection device comprising:
    an epitaxial layer of second conductivity type forming a second region;
    a first region of first conductivity type located in said epitaxial layer and having edge regions;
    a well of first conductivity type overlapping said edge regions of said first region to suppress breakdown thereof at said edge regions; and
    a third region of said second conductivity type below said first region and extending into said wells to ensure that when breakdown occurs, it occurs as area through an area of said first region enclosed by said well.

16. An integrated circuit protection device as claimed in claim 15, wherein said third region is an ion implanted region.

17. An integrated circuit protection device as claimed in claim 15, wherein said first region of first conductivity type is a deep diffusion.

* * * * *